(12) United States Patent
Boettcher et al.

(10) Patent No.: US 10,766,003 B2
(45) Date of Patent: Sep. 8, 2020

(54) PRESTERILIZABLE FILTRATION SYSTEM TO BE DISPOSED OF AFTER A SINGLE USE

(75) Inventors: Lars Boettcher, Melsungen (DE); Frank Guthof, Koerle (DE); Jan Schaefer, Edermuende (DE); Isabelle Gay, Peypin (FR)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 0 days.

(21) Appl. No.: 12/933,433

(22) PCT Filed: Mar. 13, 2009

(86) PCT No.: PCT/EP2009/001829
§ 371 (c)(1),
(2), (4) Date: Sep. 20, 2010

(87) PCT Pub. No.: WO2009/115242
PCT Pub. Date: Sep. 24, 2009

(65) Prior Publication Data
US 2011/0005984 A1 Jan. 13, 2011

(30) Foreign Application Priority Data
Mar. 20, 2008 (DE) .................. 10 2008 015 387

(51) Int. Cl.
*B01D 61/18* (2006.01)
*A61M 1/36* (2006.01)
(52) U.S. Cl.
CPC .......... *B01D 61/18* (2013.01); *A61M 1/3621* (2013.01); *A61M 1/3603* (2014.02); *B01D 2313/18* (2013.01); *B01D 2313/243* (2013.01)

(58) Field of Classification Search
None
See application file for complete search history.

(56) References Cited

U.S. PATENT DOCUMENTS

| 3,626,938 | A | | 12/1971 | Versaci |
|---|---|---|---|---|
| 4,366,051 | A | * | 12/1982 | Fischel ................. 210/96.2 |
| 4,528,093 | A | * | 7/1985 | Winer .................. 210/96.2 |
| 4,865,581 | A | * | 9/1989 | Lundquist et al. ......... 600/18 |
| 5,186,431 | A | | 12/1993 | Tamari |
| 6,712,963 | B2 | | 3/2004 | Schick |
| 7,001,513 | B2 | | 2/2006 | Bell |
| 7,052,603 | B2 | * | 5/2006 | Schick ................ 210/198.2 |
| 2002/0174721 | A1 | * | 11/2002 | Gross ..................... 73/592 |

(Continued)

FOREIGN PATENT DOCUMENTS

| WO | 97/40867 | 11/1997 |
|---|---|---|
| WO | 2001/008719 | 2/2001 |

OTHER PUBLICATIONS

International Preliminary Report on Patentability.

*Primary Examiner* — Richard C Gurtowski
(74) *Attorney, Agent, or Firm* — Gerald E. Hespos; Michael J. Porco; Matthew T. Hespos

(57) ABSTRACT

A presterilizable filtration system is provided and is to be disposed of after a single use. The system has a recirculation tank and a filtration module that are connected to each other in a circuit via a hose system that can be regulated by at least one valve. The valve has a disposable separate valve part that can be integrated in the hose system and a reusable actuator.

15 Claims, 2 Drawing Sheets

(56) References Cited

U.S. PATENT DOCUMENTS

| | | |
|---|---|---|
| 2004/0019313 A1 | 1/2004 | Childers et al. |
| 2004/0063169 A1* | 4/2004 | Kane ............................. 435/30 |
| 2004/0129649 A1* | 7/2004 | Vanhoutte .................... 210/767 |
| 2005/0109795 A1* | 5/2005 | Furey et al. ................... 222/63 |
| 2005/0230313 A1* | 10/2005 | O'Mahony et al. .......... 210/645 |
| 2005/0236329 A1* | 10/2005 | Brotherton et al. .......... 210/645 |
| 2007/0293786 A1* | 12/2007 | Wekell et al. ................ 600/561 |
| 2008/0023390 A1* | 1/2008 | Shigesada et al. ...... 210/321.84 |

* cited by examiner

PRESTERILIZABLE FILTRATION SYSTEM TO BE DISPOSED OF AFTER A SINGLE USE

BACKGROUND OF THE INVENTION

1. Field of the Invention

The invention relates to a presterilizable filtration system to be disposed of after a single use, with at least one container and at least one filtration module which are connected to each other via a hose system that can be regulated by at least one valve.

2. Description of the Related Art

U.S. Pat. No. 6,712,963 B2 and U.S. Pat. No. 7,052,603 B2 disclose filtration installations having presterilizable filtration systems to be disposed of after a single use. The filtration systems are composed of a hose system which is connected to a filtration module and which is connected to a recirculation tank via aseptic attachments. The hose system, or the medium transported in the hose system from the filtration module to the recirculation tank, can be regulated via a clamp valve.

With such a clamp valve, the hose is pressed together from the outside in order to close the hose. Although this has the advantage that the medium does not come into contact with the valve, it has the disadvantage that, particularly when using larger and thicker hoses, a great force has to be applied by the valve or by the clamping jaws acting on the hose. The closing action when squeezing the hose together can also make automatic regulation of the valve difficult.

The object of the present invention is therefore to improve the presterilizable filtration system to be disposed of after a single use, specifically in such a way that, on the one hand, it can be presterilized and packaged ready for use and, on the other hand, can be used in an automated filtration installation both at laboratory scale and also at production scale.

SUMMARY OF THE INVENTION

The object of the invention is achieved by providing a valve comprised of a disposable separate valve part that can be integrated in the hose system and a reusable actuator.

By virtue of the fact that the valve is divided into a disposable separate valve part and a reusable actuator, the separate valve part can be optimized in terms of its closure function, independently of the wall thickness of the hose.

The two-part valve can be easily used both at laboratory scale and at production scale and can be regulated via the actuator in conjunction with corresponding sensors. The valve part can be configured as a flap valve, a slide valve or, for example, a diaphragm valve.

According to a preferred embodiment of the invention, the at least one container is a recirculation tank which, with the at least one filtration module and the hose system, forms a circuit.

According to a preferred embodiment of the invention, a pump is arranged between the container or recirculation tank and the filtration module. The pump comprises a disposable pump part, which can be integrated in the hose system, and a reusable pump drive.

The known hose pumps also have the problem that they cannot in practice be employed at a large scale, particularly when relatively thick hoses are used. In production, this would in some cases lead to pumps of another type being used and to the principle of presterilization in the closed circuit being abandoned. By dividing the pump into a disposable pump part, which can be integrated in the hose system, and a reusable pump drive, the same pump type can be used relatively inexpensively at different scales while maintaining the principle of presterilization.

The pump part can be configured as an exchangeable pump head of a centrifugal pump or of a pressure piston/rotary piston pump, as is known from GB 2 440 944 A, for example.

However, it is also possible, for example, to configure the pump part as an exchangeable pump head of a diaphragm pump, as has been disclosed in DE 20 2006 020 237.4, for example.

According to a preferred embodiment of the invention, the container or recirculation tank is configured as a flexible bag. The container or the recirculation tank or flexible bag can be fixedly connected to the hose system. This has the advantage that aseptic and/or sterile attachments can be omitted, at any rate for the main connection to the recirculation tank. A subsequent liquid-tight separation of the recirculation tank or, for example, of a permeate tank can be done in a manner known per se by severing the connection hose using a welding appliance, the two hose ends being closed by welding.

In a preferred embodiment of the invention, the container or recirculation tank is fitted with a gas admission/gas removal filter with pressure sensor with reusable transducer or with a safety valve which protects the container or recirculation tank from mechanical destruction by inadmissible excess pressure or from collapse.

According to another preferred embodiment of the invention, the permeate outlet of the at least one filtration module and a permeate tank are connected fixedly via a permeate hose line. A valve composed of a disposable separate valve part and of a reusable actuator can be arranged in the permeate hose line.

According to another preferred embodiment of the invention, measuring points are arranged in the hose system and/or in the permeate hose line, which measuring points are each divided into a disposable measuring, integrated in the hose system and/or in the permeate hose line, and a reusable transducer.

The parts of the measuring points that come into contact with product or media can therefore be easily presterilized and disposed of together with the whole hose system. The transducers or transmitters remain in the filtration installation. The measuring cells can be configured as sensors for measuring pressure, flow, temperature, filling level, pH, conductivity, optical density, oxygen partial pressure and UV, and their signals can be sent to a computing and controlling unit via the transducers.

According to another preferred embodiment of the invention, the filtration module is configured as a dead-end filtration module. The filtration modules can in particular be in the form of filter capsules with hollow fiber membranes, flat membranes, membrane adsorbers and depth filters for the ultrafiltration and microfiltration range, including virus filters.

According to another preferred embodiment, the filtration module is configured as a crossflow filter with tangential feed. The crossflow filter is configured, for example, as a stack of membrane cartridges. The filtration modules can in particular be in the form of membrane cartridges with hollow fiber membranes, flat membranes, membrane adsorbers and depth filters for the ultrafiltration and microfiltration range, including virus filters.

The filtration modules are configured as disposable articles to be discarded after a single use.

With the aid of external units, further media can be delivered to the system via aseptic standard attachments on the container or recirculation tank. The presterilizable filtration system can be supplied to the operator in a sterilized form and packaged in a sterile atmosphere. The filtration system can be fitted into the filtration installation and operated under aseptic conditions. In this way, filtration can be performed under aseptic or sterile conditions using disposable products, and, when the filtration is completed, all the structural parts coming into contact with product can be disposed of as a closed system. Escape of media from the system is therefore excluded for the protection of the operator. The rest of the filtration installation is configured for data recording and viewing, for example via a screen, which is preferably configured as a touch-screen, and the mechanical supply units are fitted, in successive production cycles, with a new sterile filtration system.

All the measuring points or measuring cells can be supplied to the operator in a form precalibrated for the filtration system.

The presterilizable filtration system can be supplied as a closed system in sterile packaging. All the components of the filtration system that can be supplied to the customer are sterilizable, the sterilization preferably being carried out with gamma rays.

Further features of the invention will become clear from the following detailed description and from the attached drawings in which preferred embodiments of the invention are illustrated by way of example.

BRIEF DESCRIPTIONS OF THE DRAWINGS

DETAILED DESCRIPTION OF THE PREFERRED EMBODIMENT

Figure 1:
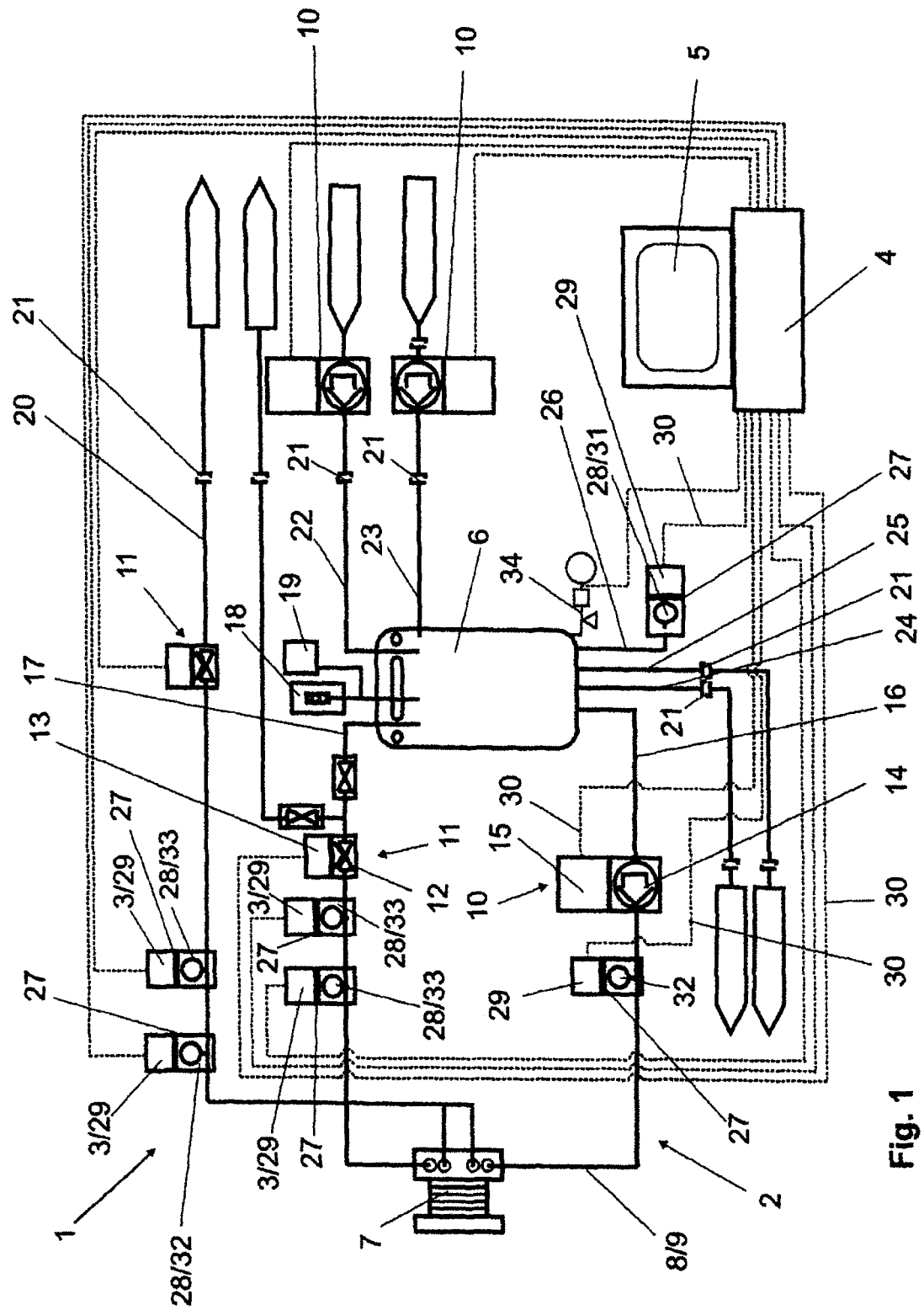
FIG. 1 is a schematic representation of a filtration installation.
Figure 2:
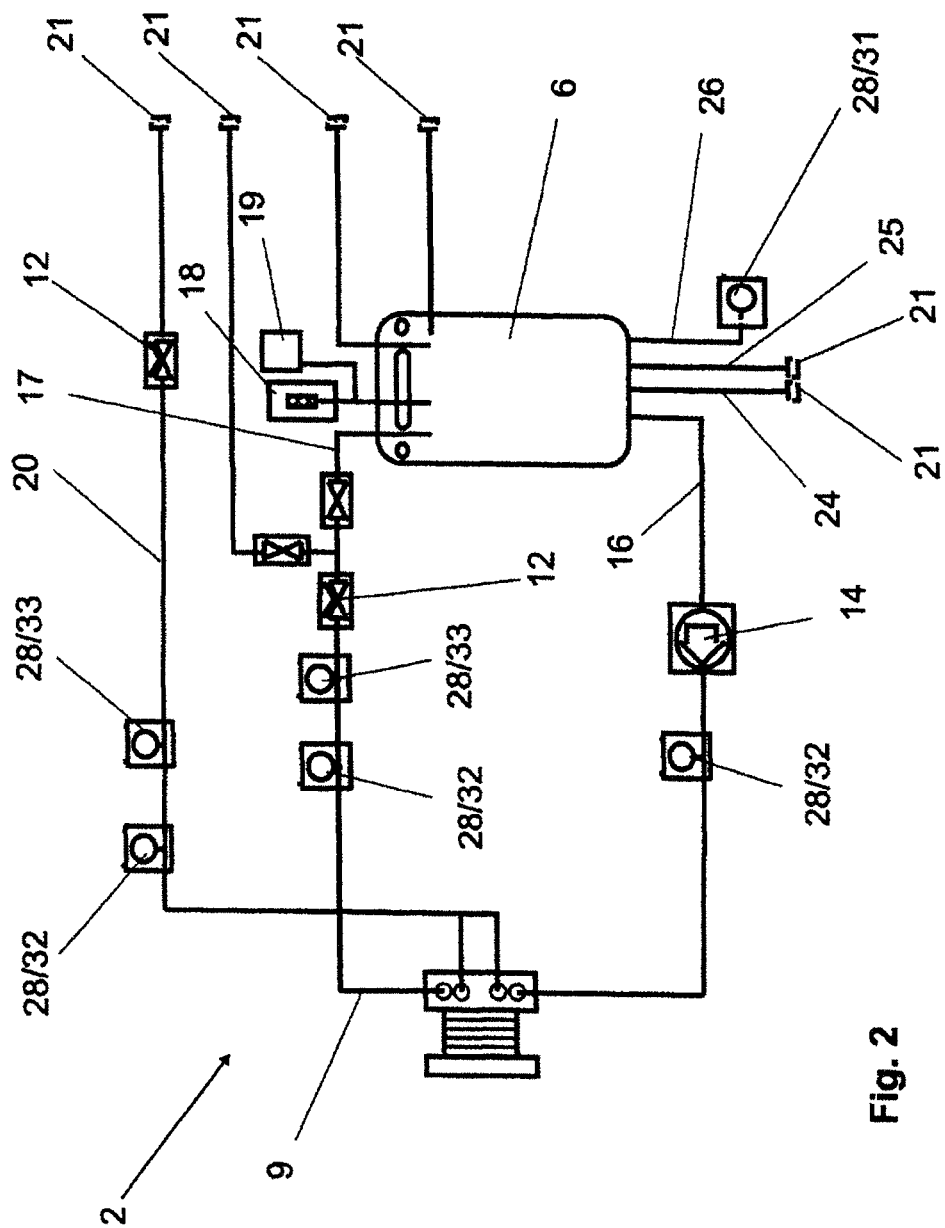
FIG. 2 is a schematic representation of the presterilizable filtration system from FIG. 1.

The filtration installation 1 is basically composed of a presterilizable filtration system 2 to be disposed of after a single use, and of reusable installation parts 3 that include a computing and controlling unit 4 with a screen 5.

The filtration system 2 is designed to be disposed of after a single use and basically comprises a recirculation tank 6 and a filtration module 7 which are connected to each other in a circuit 9 via a hose system 8. A pump 10 is arranged between the recirculation tank 6 and the filtration module 7 in order to circulate the medium that is to be filtered. A valve 11 that can be controlled by the computing and controlling unit 4 is arranged between the filtration module 7 and the recirculation tank 6 in the hose system 8 or circuit 9. The valve 11 is composed of a separate valve part 12, with a variable passage through which the medium is conveyed, and of an actuator 13 which can be connected to the valve part 12 and which forms a reusable installation part 3. The actuator 13 is connected to the computing and controlling unit 4 and is controlled by the latter. The valve part 12 is configured, for example, as a flap valve (not shown).

The pump 10 is likewise configured in two parts and is composed of a disposable pump part 14, which can be integrated in the hose system 8, and of a reusable pump drive 15, which forms a reusable installation part and which is likewise connected to the computing and controlling unit 4 and is controlled by the latter. The pump part 14 is configured, for example, as a pump head (not shown) of a centrifugal pump.

The recirculation tank 6 is configured as a flexible bag and is fixedly connected to a feed hose 16 that leads to the pump part 14, and to a return hose 17 that leads back from the filtration module 7 through the circuit 9.

The filtration module 7 is connected to the circuit 9. The permeate outlets of the filtration module 7 are connected to a permeate hose line 20, which leads to a permeate tank (not shown). A separate valve part 12 and/or a further controllable valve 11 is integrated in the permeate hose line 20. A sterile connector 21 to the permeate tank (not shown) is arranged in the permeate hose line 20, via which sterile connector 21 the permeate tank can be coupled in a sterile manner or can be exchanged in a sterile or at least aseptic manner. The permeate tank is preferably connected fixedly to the permeate hose line 20. The recirculation tank 6 has, at its upper end, two hose connections 22, 23 which are closed at their ends by sterile connectors 21 and through which media can be conveyed, if appropriate with the aid of further pumps 10. At its lower end, the recirculation tank 6 has two further hose connections 24, 25 which are likewise closed off by sterile connectors 21 and to each of which containers (not shown) can be connected in order to take up medium from the recirculation tank 6. A further hose 26 arranged at the lower end of the recirculation tank 6 is connected to a measuring point 27 which is divided into a disposable measuring cell 28, which is integrated in the hose system 8, and a reusable transducer 29. The transducer 29 is in each case connected via a signal line 30 to the computing and controlling unit 4.

The container 6 or recirculation tank is fitted with a gas admission/gas removal filter 18 with a safety valve 19.

The measuring cell 28 integrated in the hose 26 is configured as a temperature sensor 31. In the circuit 9, between pump 10 and filtration module 7, there is a further measuring point 27 whose measuring cell 28 is configured as a pressure sensor 32. Two further measuring points 27 are moreover arranged in the circuit 9 between the controllable valve 11 and the filtration module 7. One measuring cell 28 is configured as a pressure sensor 32, and a further measuring cell 28 is configured as a flow meter 33.

Two measuring points 27 are likewise arranged in the permeate hose line 20, the measuring cell 28 of one being configured as a pressure sensor 32, and the measuring cell 28 of the other measuring point 27 being configured as a flow meter 33. In the direction toward the sterile connector 21, a further controllable valve 11 is arranged in the permeate hose line 20. The recirculation tank 6 is connected to a weighing module 34 which determines the weight in the recirculation tank 6 and forwards this weight to the computing and controlling unit 4. The signal from the weighing module 34 can also be used as a filling level signal.

The filtration system 2 can be presterilized as a fully interconnected overall system and can be supplied in sterile outer packaging. The operator then simply has to remove the filtration system 2 from its outer packaging (not shown) and fit it into the filtration installation 1 and connect the disposable parts of the valves 11, pumps 10 and measuring points 27 to their counterparts that remain in the filtration installation 1.

When filtration is complete, all the structural parts of the filtration system 2 that come into contact with product can be disposed of as a closed system.

All the measuring cells 28 of the measuring points 27 are supplied in precalibrated form to the operator.

The invention claimed is:

1. A filtration system, comprising:
a pre-sterilized subsystem (2) that includes:

at least one disposable Container (6);
at least one disposable filtration module (7);
a disposable hose system (8) connecting the at least one container (6) and the at least one filtration module (7);
a disposable pump part (14) integrated into the hose system (8) between the at least one container (6) and the at least one filtration module (7);
a disposable, valve part (12) integrated in the hose system (8) and having a variable passage; and
a plurality of disposable measuring cells (28) integrated into the hose system (8); and
a reusable filtration installation (1) that includes:
a reusable pump drive (15) removably associated with the disposable pump part (14) for selectively operating the disposable pump part (14) to control flow through the hose system (8);
a reusable actuator (13) removably associated with the disposable valve part (12) and operating the disposable valve part (12) for selectively varying the passage of the disposable valve part (12) to control flow through the hose system (8);
reusable transducers (29) removably associated respectively with the disposable measuring cells (12); and
a controlling unit (4) connected to the reusable actuator (13), to the reusable transducers (29) and to the reusable pump drive (15) for controlling the disposable pump part (14) and for controlling the reusable actuator (13) and thereby controlling the disposable valve part (12) of the valve (11) and for receiving information from the measuring cells (28), and
wherein the at least one container (6), the at least one filtration module (7), the hose system (8), the disposable valve part (12), disposable measuring cells (28) and the disposable pump part (14) are prepackaged in a sterile manner for connection to the reusable actuator (13), the reusable pump drive (15) and the reusable transducers (29).

2. The filtration system according to claim 1, wherein the at least one container (6) is a recirculation tank which, with the at least one filtration module (7) and the hose system (8), forms a circuit (9).

3. The filtration, system according to claim 1, wherein the disposable valve part (12) is as a flap valve, diaphragm valve, ball valve, seat valve or slide valve.

4. The filtration system according to claim 1, wherein the disposable pump part (14) is an exchangeable pump head of a pressure piston pump, rotary piston pump, centrifugal pump or diaphragm pump.

5. The filtration system according to claim 1, wherein the at least one container (6) is a flexible bag.

6. The filtration system according to claim 1, wherein the at least one container (6) is connected to the hose system (8) via a fixed connection, the hose system being configured to be cut by a welding appliance for separating the at least one container (6) from the hose system (8) in a liquid-tight manner.

7. The filtration system according to claim 1, wherein the at least one filtration module (7) has a permeate outlet, and the hose system further comprising a permeate hose line (20) fixedly connected to the permeate outlet for delivering permeate to a permeate tank.

8. The filtration system according to claim 7, further comprising a second a second disposable valve part (12) integrated in the permeate hose line (20) and a second reusable actuator (13) removably associated with the second disposable valve part (12), the second reusable actuator (13) being configured for operating the disposable valve part (12) for selectively varying the passage of the second disposable valve part (12) to control flow of permeate through the permeate hose line (20).

9. The filtration system according to claim 1, wherein the at least one filtration module (7) is dead-end filtration module.

10. The filtration system according to claim 9, wherein the dead-end filtration module (7) is a filter capsule.

11. The filtration system according claim 2, wherein the at least one filtration module (7) is a crossflow filter with tangential feed.

12. The filtration system according to claim 11, wherein the crossflow filter (7) is a stack of membrane cartridges.

13. The filtration system according to claim 1, wherein the at least one filtration module (7) contains filtration membranes in an ultrafiltration or microfiltration range and comprising hollow fibers, flat membranes or membrane adsorbers.

14. The filtration system according to claim 1, wherein the at least one container has a disposable safety valve.

15. The filtration system according to claim 1, wherein all parts of the filtration system are formed from materials that can be sterilized with gamma rays.

* * * * *